United States Patent [19]

Williamitis

[11] Patent Number: 4,904,433

[45] Date of Patent: Feb. 27, 1990

[54] METHOD FOR DIE RELEASE DURING CATHETER TIPPING

[75] Inventor: Victor A. Williamitis, Dayton, Ohio

[73] Assignee: Becton, Dickinson and Company, Franklin Lakes, N.J.

[21] Appl. No.: 315,967

[22] Filed: Feb. 27, 1989

[51] Int. Cl.$^4$ .............................................. B29C 57/00
[52] U.S. Cl. .................................. 264/130; 264/138; 264/163; 264/320; 604/265
[58] Field of Search ............... 264/130, 320, 322, 138, 264/163; 604/265

[56] References Cited

U.S. PATENT DOCUMENTS

| | | | |
|---|---|---|---|
| 3,574,673 | 4/1971 | Schweiger | 428/450 |
| 4,588,398 | 5/1986 | Daugherty et al. | 604/265 |
| 4,661,300 | 4/1987 | Daugherty | 264/320 |
| 4,664,657 | 5/1987 | Williamitis | 604/265 |

*Primary Examiner*—James Lowe
*Attorney, Agent, or Firm*—Richard E. Brown

[57] ABSTRACT

A method for catheter tipping including applying to a catheter blank a layer of a noncuring aminoalkyl terminated polysiloxane lubricant, mounting the lubricated blank on a mandrel and advancing the mandrel-catheter assembly into a heated die so that the die causes the heated tip of the blank to assume the shape of the die. The catheter may then be cut beyond the shaped tip and easily removed from both the die and the mandrel.

8 Claims, No Drawings

METHOD FOR DIE RELEASE DURING CATHETER TIPPING

BACKGROUND OF THE INVENTION

1. Field of the Invention

This invention relates to catheter tipping, and more particularly relates to facilitating release of a tipping die from a tipped catheter.

2. Background of the Invention

Intravenous (I.V.) catheters are extensively used in medical applications for directing blood, plasma, or other fluids into the circulatory system of a patient. While I.V. catheters are available in several different types, one common type of catheter is constructed so as to be mounted upon a relatively long, hollow cannula with a slight friction fit. A hub is attached at one end of the catheter and is designed so as to be connectable with and detachable from an I.V. fluid supply line. To insert the catheter into the patient, the cannula and catheter together are inserted through the patient's skin, whereupon the cannula may be withdrawn, leaving the catheter in place.

Untipped catheter tubing as extruded (hereinafter referred to as blank) is unsuitable for insertion through the skin of the patient because it has blunt ends which cause pain, trauma and irritation to the surrounding tissue. Accordingly, it is conventional to provide a tapered tip for insertion. Further, if the catheter is to remain in position for a long period of time, it is more comfortable for the patient if it is made of a relatively soft pliable material. Because it is soft and pliable, the catheter is generally used with a removable introducer needle fitted coaxially within the catheter in order to puncture the skin and penetrate the vessel. The introducer needle needs to project slightly beyond the end of the catheter so that, shortly after the introducer needle has pierced the skin of the patient, the catheter may then pass through the same perforation. Once the catheter has been slid along the needle into position, the introducer needle can then be removed by coaxially withdrawing the needle from within the inserted catheter.

It has been a problem with devices of this type to produce a catheter having a tapered tip which permits insertion over the introducer needle. More specifically, the catheter body has to be of high strength and thin wall in order to permit maximum fluid flow yet the tip requires a specific design to permit ease of introduction along with the needle.

Daugherty et al. discloses in U.S. Pat. No. 4,588,398 a catheter tip configuration for over-the-needle polyurethane catheters having a steep bevel at the distal end of the tip and a shallow bevel immediately above the steep bevel. The patented catheter tip and whole catheter are lubricated with a mixture of DC 360® polydimethylsiloxane (Dow Chemical) and Dow 4-4159MDX (a moisture curable amine terminated polysiloxane disclosed in U.S. Pat. No. 3,574,673, hereinafter referred to as MDX) to ease catheter insertion through a venipuncture created by the needle. In U.S. Pat. No. 4,661,300, hereby incorporated by reference, Daugherty discloses an apparatus for catheter tipping which includes a mandrel and a heated die. A silicone prelubricated catheter blank on the mandrel is shaped by the die and cut externally of the die to provide the tip.

Williamitis et al., in U.S. Pat. No. 4,664,657, lubricates a catheter assembly at the cannula (needle) tip with a polydimethylsiloxane having a viscosity in the range of 60,000 to 2,500,000 centistokes (ctsk). On mating of the cannula by interference fit with a catheter, reduction in the development of time-temperature adhesion between the catheter and cannula tip is achieved.

For catheter tipping, the purpose of the lubricant is to prevent catheter adhesion to the forming die and mandrel at the near melt temperature of tipping. While it is known in the art to lubricate cannulas, catheters and dies, the lubricants which have been disclosed for this purpose have various deficiencies.

Polydimethylsiloxane silicone oils have been used as lubricants in catheter tipping. These products, however, have the disadvantage of being easily wiped away. Formulas based on the organopolysiloxanes described in U.S. Pat. No. 3,574,673 and disclosed for catheter tipping in U.S. Pat. No. 4,588,398, have hitherto been the best die release agent. These products, such as MDX, are copolymers of alkylamine modified methoxysiloxanes and undergo room temperature vulcanization (RTV) to a gelatinous film. These organosiloxanes are referred to as gelling siloxanes and, depending on ambient humidity, require at least a four-hour precure of the coating applied to a catheter blank prior to tipping, and further require from two to ten days for full cure. In addition, solvent solutions of MDX, used for application of the MDX to catheter blanks by dipping, quickly turn cloudy due to precipitated polymer from reaction of the MDX with humidity in the air. During a tipping operation, these solutions must be replaced frequently to prevent buildup of cured MDX on the tipping die, which is time consuming, wasteful and costly. These constraints are a severe limitation to use of the formulations of U.S. Pat. No. 3,574,673 for catheter tipping.

Thus, there is a need in the art for a method for tipping polyurethane catheters which avoids the limitations imposed on prior art tipping methods by the hitherto disclosed die releasing lubricants.

SUMMARY OF THE INVENTION

The method of the present invention is directed to forming tapered tips on polyurethane catheters for ease and comfort of insertion into a patient. A catheter blank is coated with a noncuring polysiloxane lubricant terminated with an active functional group. The coated blank is advanced to engage a heated die which causes the polyurethane to soften. The softened tip of the polyurethane catheter blank assumes the shape of the die. The shaped tip is cut, and the catheter separated from the die.

In a preferred embodiment of the invention, the lubricant is applied to the catheter blank by dipping the blank into the lubricant or preferably into a solution of the lubricant in a nontoxic solvent so that both the outside wall and the lumen wall of the blank receives a coating of the lubricant. The blank is then mounted onto a mandrel and engaged to the heated die by application of pressure.

Preferred lubricants are polydialkylsiloxanes terminated with a carboxyalkyl or aminoalkyl group. The most preferred lubricants are polydimethylsiloxanes having a viscosity about 1,000 to 2,000 ctsk. which are terminated with an aminopropyl group.

Thus, when tipped by the method of the invention using the noncuring lubricants disclosed herein, the tipped catheter releases easily and quickly from the die and the mandrel. The lubricant is nontoxic, of good flowability for application by neat or solvent solution dipping, and, because it is noncuring, can be coated onto the blank and the tipping operation conducted with no waiting during a precure period. Also, because of its noncuring nature, the lubricant does not partially cure and precipitate in the dipping solution and thus does not undergo any chemical or physical changes and does not substantially accumulate on the die during a continuous tipping operation. Longer die life before cleaning or replacement and less down time of the tipping apparatus result. In contrast, curing lubricants must be precured prior to tipping to prevent curing on the die which causes buildup on the die. Because of the many salubrious properties of the noncuring lubricants disclosed, a higher percentage of the tips prepared by the method of the invention meet the rigorous product specifications defined to ensure maximum patient safety and comfort.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

The catheter tubing to be tipped by the method of the present invention may be any thermoplastic polymer suitable for conventional extrusion into tubing, such as polyolefin, fluorinated polyolefin, polyvinylchloride, polystyrene and the like. Preferred polymers are polyurethanes which combine side wall strength and rigidity when cool and dry with softening and flexibility due to body temperature and water absorption when wet, as for example when in contact with blood. Because of this particular combination of properties, polyurethane catheters provide ease of insertion into a patient's vein due to the rigidity when dry and ease of following a tortuous vein due to the softening after insertion. In the present invention, the term polyurethane is intended to include all segmented polymers containing urethane linkages such as polyurethaneureas and polyurethanes containing polysiloxane blocks.

Extrusion of polyurethanes into tubing is conventional, and any tubing guage size from 26 to 6 suitable for catheter use is contemplated to fall within the scope of the invention. Preferred polyurethane catheters to be tipped by the method of the invention are about 24 to 14 gauge.

Tipping of polyurethane catheters has been a problem in the art. In accordance with the present invention, an improved method for catheter tipping includes applying a noncuring polar polysiloxane lubricant terminated with an active functional group to a catheter blank prior to tipping. It has been found that the lubricants disclosed herein, when applied to a blank catheter, form a stable firmly adsorbed film on a tipping die during the tipping operation but release the tipped catheter from the die easily and cleanly after tipping. Further, the tipped catheter also separates easily from the forming and cut off mandrel.

The lubricants contemplated by the present invention are noncuring polysiloxanes terminated by active polar groups, and may be represented by the formula

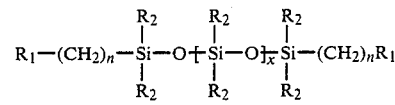

wherein $R_1$ may be $NH_2$,

and COOH, $R_2$ may be lower alkyl of 1 to 4 carbon atoms, n may be 2 to 4, and x is an integer sufficient to give the lubricant a viscosity of about 10 to 2,000,000 ctsk. In preferred lubricants, $R_1$ is $NH_2$ or COOH, $R_2$ is $CH_3$ and the viscosity is 100 to 100,000 ctsk. The most preferred lubricants are aminopropyl terminated polydimethyl siloxanes of viscosity 300 to 25,000 ctsk. These lubricants are known in the art and are commercially available from Petrarch Systems, Bristol, Pennsylvania. The invention will henceforth be described in terms of the commercial aminopropyl terminated Petrarch lubricant PS513 of viscosity 2,000 ctsk.

Blank catheters to be tipped by the method of the invention may be dipped into the neat lubricant or preferably may be dipped into a solution of PS513 in a solvent. Preferred solvents are fire safe, volatile nontoxic solvents such as for example isopropanol or FREON ® TF or mixtures thereof. The time of dipping is not critical, and it is evident that the PS513 may equally well be applied to the catheter blank by other procedures, such as brushing or spraying. If desired, the solvent may be removed after lubricant application by ambient evaporation or by warming. Excess lubricant may be removed from the blank catheter lumen simply by dripping away or preferably may be blown out with a light puff of air.

After lubrication, the blank catheter tubing to be tipped is mounted onto a mandrel. It is evident that the fit between the tubing and the mandrel is lubricated by the PS513 on the lumen wall of the tubing. The tubing-mandrel assembly may then be advanced until the tubing engages the proximal side of a die which has been preheated to a temperature sufficient to soften the polyurethane, usually about 35° to 230° C., preferably about 150° to 200° C. An apparatus as that described in U.S. Pat. No. 4,661,300, may be used. When the tubing has engaged the die, the tubing-mandrel assembly may be further advanced, preferably by application of sufficient pressure to the assembly, so that the die cuts the formed catheter tip to the shape of the dye, scraps of cut polymer exiting from the distal side of the die.

The catheter thus tipped is cut cleanly on the distal side of the die, and the tipped catheter easily and quickly removed from the die and the mandrel due to the "release" effectiveness of the noncuring lubricant.

For use in high temperature tipping of polyurethane catheters, the preferred lubricants have several attributes. Since the catheters are to be inserted into a patient's body, their nontoxicity is essential. Substantially instantaneous release from die and mandrel is achieved with minimal lubricant. Absorption of the very thin lubricated film insures that the lubricant does not interfere with the formation of the tip shape. Dipping solutions are stable and do not become cloudy because of the noncuring nature of the lubricant. It is appreciated by those skilled in the art that, when a die is exposed repeatedly to lubricated blank catheters, some buildup of heat deteriorated lubricant on the die takes place, particularly if the lubricant undergoes any change, such as curing during the tipping operation. This buildup, which adversely affects release or alters the shape of the die and with it the shape of the tipped catheter, is referred to in the art as die contamination. The time that a die can be used continuously for tipping before contamination forces down time of the tipping apparatus for die cleaning or replacement is generally referred to as die life. Die life, of course, should be as long as possible.

By eliminating the requirement for a precure period, the method of the invention is admirably suited for automation. In an automated process, it is particularly desirable if the die life is at least as long as a working shift so that the down time can occur between shifts.

The amino alkyl substituted polysiloxane lubricant of the present invention is markedly superior to the prior art silicone lubricants of U.S. Pat. Nos. 4,661,300 and 4,664,657 and the curing lubricants of U.S. Pat. Nos. 3,574,673 and 4,588,398 for catheter tipping. In particular, catheters tipped by the method of the invention are more uniform than catheters tipped using prior art lubricants. In general, catheters tipped using nonpolar silicone oil lack the consistent smooth surfaces of catheters tipped by the method of the invention. On the other hand, a substantial number of catheters tipped with curing lubricants are cloudy. Curing lubricants also cause significant die contamination and shorter die life due to precipitation and moisture curing in the dipping solution. In the art, this problem has routinely required frequent and wasteful dumping of cloudy dipping solutions. The extended precure itself is a disadvantage in production operations by requiring "bank" space, preventing compact in-line flow and exposing catheters unnecessarily to extra airborne contamination.

The following Example is provided to further illustrate the invention but is not intended in any way to be limitative of the invention.

EXAMPLE

Polyurethane catheter blanks of 14,16,20,22 and 24 guage were lubricated in groups of 96 as indicated in Table I wherein all percentages are by weight. The lubricated catheters were tipped at 175° C. with the apparatus of U.S. Pat. No. 4,661,300 to form a 30° bevel at the distal end of the catheter tip and a 4° bevel thereabove. The tipped catheters were released from the die and mandrel, visually examined under 30x magnification and judged for accuracy of bevels, smoothness, appearance of the cuts, presence of uncut "whiskers," clarity, color and presence of cracks. The effectiveness of the lubricant is given in Table II as the percentage of catheter tips judged to be satisfactory in all parameters.

TABLE I

Lubricant A . . . 0.25% MDX and 0.22% DC 360* each of 1,000 cstk. in 30% isopropanol and 70% FREON ® TF.**
Lubricant B . . . 0.5% PS-513 of 2,000 cstk. in FREON ® TF.
Lubricant C . . . 0.25% PS-513 of 2,000 cstk. in FREON ® TF.
Lubricant D . . . 0.5% DC 360 of 12,500 cstk. in FREON ® TF.
Lubricant E . . . 0.5% DC 360 of 1,000,000 cstk. in FREON ® TF.
Lubricant F . . . 0.5% DC 360 of 1,000 cstk. in FREON ® TF.

TABLE I-continued

Lubricant G . . . 0.5% PS 563*** of 800 to 1,200 cstk. in FREON ® TF.
Lubricant H . . . 0.5% PS-510**** of 50 ctsk. in FREON ® TF.

*Dow Corning medical grade polydimethylsiloxane
**Catheter blank lubricated and set aside for four hour precure prior to tipping
***carboxypropyl terminated polydimethylsiloxane
****aminopropyl terminated polydimethylsiloxane

TABLE II

| Lubricant | Gauge | Effectiveness | |
|---|---|---|---|
| A | 14 | 73/96 | |
|   | 16 | 87/96 | |
|   | 20 | 88/96 | |
|   | 22 | 79/96 | |
|   | 24 | 66/96 | |
|   |    |       | average 81.9% |
| B | 14 | 88/96 | |
|   | 16 | 90/96 | |
|   | 20 | 90/96 | |
|   | 22 | 85/96 | |
|   | 24 | 77/96 | |
|   |    |       | average 90.1% |
| C | 14 | 83/96 | |
|   |    |       | average 86.5% |
| D | 14 | 85/96 | |
|   | 16 | 84/96 | |
|   | 20 | 80/96 | |
|   | 22 | 82/96 | |
|   |    |       | average 82.8% |
| E | 16 | 40/96 | |
|   |    |       | average 41.6% |
| F | 16 | 60/96 | |
|   |    |       | average 62.5% |
| G | 14 | 86/96 | |
|   |    |       | average 89.6% |
| H | 14 | 82/96 | |
|   |    |       | average 85.4% |

Thus, the invention using the disclosed noncuring lubricant for die release provides a substantially higher percentage of fully satisfactory catheter tips which are easily removed from the die and of excellent shape, color and appearance by a method which eliminates precure, substantially improve die life and reduces down time because of die contamination.

What is claimed is:

1. A method for forming a shaped tip on a polyurethane catheter comprising:
   (a) applying a film of a noncuring aminoalkyl terminated polysiloxane lubricant to an untipped polyurethane catheter tubing;
   (b) mounting said tubing onto a mandrel;
   (c) engaging said tubing to a die heated to a temperature sufficient to soften said polyurethane and cause the tip of said tubing to assume the shape of said die; and
   (d) cutting the shaped catheter tubing to give a tipped catheter and removing same from said die and from said mandrel.

2. The method of claim 1 wherein said polysiloxane lubricant is selected from the group having the formula

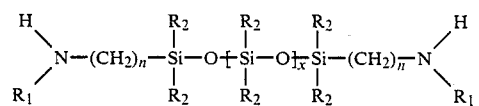

wherein $R_1$ is H or $R_2$, $R_2$ is lower alkyl of 1 to 4 carbon atoms, n is 2 to 4 and x may be an integer sufficient to give the lubricant a viscosity of about 100 to 100,000 ctsk.

3. The method of claim 1 wherein said tubing has a gauge of 26 to 6.

4. The method of claim 1 wherein said temperature is about 35° to 230° C.

5. The method of claim 1 wherein said engaging step includes applying pressure to the tubing mounted on said mandrel.

6. A method for forming a shaped tip on a plastic catheter comprising:
(a) applying a film of a noncuring polysiloxane lubricant terminated with an active functional group to an untipped plastic catheter tubing;
(b) engaging said tubing to a die heated sufficiently to soften said plastic so that the softened tip of said tubing assumes the shape of said die; and
(c) cutting the shaped tubing and removing same from said die to give a catheter having a shaped tip.

7. The method of claim 6 wherein said polysiloxane is selected from the group having the formula

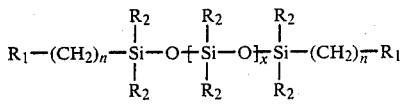

wherein $R_1$ may be $NH_2$,

and COOH, $R_2$ may be lower alkyl of 1 to 4 carbon atoms, n may be 2 to 4, and x is an integer sufficient to give the lubricant a viscosity of about 10 to 2,000,000 ctsk.

8. A method for forming a shaped tip on a polyurethane catheter comprising:
(a) applying a layer of a noncuring aminopropyl terminated polysiloxane lubricant having a viscosity of about 1,000 to 2,000 ctsk to an untipped polyurethane catheter tubing;
(b) mounting said tubing onto a mandrel;
(c) advancing said mandrel and tubing to a die heated to about 100° to 200° C.;
(d) applying pressure to said tubing so that said tubing engages said heated die, softens and assumes the shape of said die;
(e) cutting the shaped catheter tubing to give a tipped catheter; and
(f) removing said tipped catheter from said die and from said mandrel.

* * * * *